United States Patent [19]

Sheng et al.

[11] 4,049,724

[45] Sept. 20, 1977

[54] OSMIUM CATALYZED ORGANIC HYDROPEROXIDE HYDROXYLATION OF OLEFINIC COMPOUNDS

[75] Inventors: Ming N. Sheng, Cherry Hill, N.J.; Walter A. Mameniskis, Drexel Hill, Pa.

[73] Assignee: Atlantic Richfield Company, Los Angeles, Calif.

[21] Appl. No.: 620,436

[22] Filed: Oct. 7, 1975

Related U.S. Application Data

[63] Continuation of Ser. No. 417,681, Nov. 20, 1973, abandoned.

[51] Int. Cl.$^2$ .................... C07D 307/89; C11C 1/00; C07C 29/02
[52] U.S. Cl. ................ 260/635 H; 260/413; 260/346.3
[58] Field of Search ............... 260/635 H, 413, 346.3

[56] References Cited

U.S. PATENT DOCUMENTS

| | | | |
|---|---|---|---|
| 2,437,648 | 3/1948 | Milas | 260/635 H |
| 2,773,101 | 12/1956 | Smith et al. | 260/635 H |
| 2,813,130 | 11/1957 | Keeler et al. | 260/635 H |
| 2,833,787 | 5/1958 | Carlson et al. | 260/635 H |
| 3,317,592 | 5/1967 | Maclean et al. | 260/635 H |
| 3,488,394 | 1/1970 | Cummins | 260/635 H |

*Primary Examiner*—Joseph E. Evans
*Attorney, Agent, or Firm*—Delbert E. McCaslin

[57] ABSTRACT

Method for preparing polyols such as diols and triols by the homogeneous catalytic hydroxylation of an olefinic compound by contacting the olefinic compound with an organic hydroperoxide in an aqueous solution at an initial pH above 8 in the presence of a catalytic amount of a water soluble osmium compound as the catalyst.

7 Claims, No Drawings

OSMIUM CATALYZED ORGANIC HYDROPEROXIDE HYDROXYLATION OF OLEFINIC COMPOUNDS

This is a continuation of application Ser. No. 417,681 filed Nov. 20, 1973, now abandoned.

BACKGROUND OF THE INVENTION

It is well known from the technical literature including patents that olefins can be effectively oxidized with osmium compounds, particularly osmium tetroxide, to their corresponding diols when the reaction is carried out with catalytic amounts of osmium tetroxide and a stoichiometric amount of a strong oxidizing agent. The oxidizing agents which have been proposed and used include the alkali metal chlorates and hypochlorites, potassium ferricyanide and hydrogen peroxide. For example, in U.S. Pat. No. 2,414,385 to Milas, unsaturated compounds having an alcohol or ether group are contacted with an initially substantially anhydrous solution of hydrogen peroxide in an inert organic solvent medium in the presence of a catalyst such as an oxide of osmium. In U.S. Pat. No. 2,773,101 to Smith et al a method is shown for recovering osmium tetroxide from a process of hydroxylating an olefinic compound with hydrogen peroxide in the presence of osmium tetroxide. The patentees state, although no data or examples are given, that inorganic peroxides such as sodium and barium peroxides or organic peroxides such as tertiary butyl peroxide, tertiary butyl hydroperoxide or benzoyl peroxide can be used instead of the hydrogen peroxide. Certainly these are not all equivalent oxidizing agents since only the tertiary butyl hydroperoxide is sufficiently water soluble and/or stable to be used as the oxidation agent.

Oxidation of $Os^{+6}$ to $Os^{+8}$ with molecular oxygen in aqueous alkaline solutions has also been reported, thus under these conditions olefins are oxidized to their corresponding diols at a pH in the range of 8.5 – 10.5 and to oxalic acid at a pH of 12.5.

The reaction rate is slow, however, and the reaction ceases when the molar ratio of diol to osmium tetroxide exceeds 2. The same limitation applies to allyl alcohol, glycerol, acetone and formic acid.

SUMMARY OF THE INVENTION

It has now been found that olefinic compounds can be hydroxylated to organic compounds having two or more hydroxyl groups such as diols, triols, and other polyols by employing an organic hydroperoxide such as tertiary butyl hydroperoxide in an aqueous solution at an initial pH about 8 and generally in the range of from 8 to 12 in the presence of catalytic amounts of osmium in the form of a water soluble osmium compound and in the presence of a buffering agent.

The advantages for such a process are numerous, for example, organic hydroperoxides, in particular tertiary butyl hydroperoxide, is considerably more stable than hydrogen peroxide and other inorganic and organic oxidizing agents described in the literature and in addition it is much less costly and can be shipped safely, thus avoiding the necessity of producing the oxidizing agent at the site of use.

The instant process also gives much faster reaction rates and higher concentration of the polyols than processes employing oxidation with molecular oxygen for example.

It is an object of this invention therefore, to provide a method for the preparation of diols, triols and other polyols by the hydroxylation of olefinic compounds.

It is another object of this invention to provide a method for the hydroxylation of olefinic compounds employing an organic hydroperoxide hydroxylating agent, a water soluble osmium-containing catalyst and a buffering agent.

It is another object of this invention to provide a method for the hydroxylation of olefinic compounds to produce diols, triols and other polyols employing an aqueous solution of tertiary butyl hydroperoxide and a water soluble osmium compound and a buffering agent with an initial pH of from 8 to 12 of the aqueous solution which methods gives faster reaction rates and higher diol, triol and other polyol concentrations than previously described methods.

Other objects of this invention will be apparent from the description of the invention which follows and from the claims.

DESCRIPTION OF THE INVENTION

The olefinic compounds which can be hydroxylated in accordance with this invention are those preferably having from 2 to 18 carbon atoms, including mono-olefinic compounds, diolefinic or polyolefinic compounds, both conjugated and non-conjugated, hydroxy-substituted olefinic compounds, olefinically unsaturated aliphatic carboxylic acids and anhydrides, such as oleic acid, 1,2,3,6-tetrahydrophthalic anhydride and the like. The preferred olefinic compounds are allyl alcohol and propylene.

Although theoretically any organic hydroperoxide might be operable the preferred organic hydroperoxides are stable and water soluble and the most preferred are tertiary butyl hydroperoxide and tertiary amyl hydroperoxide. Since frequently these hydroperoxides are made by the molecular oxygen oxidation of the corresponding hydrocarbon there is also produced the corresponding alcohol. For example when isobutane is oxidized with molecular oxygen there is produced tertiary butyl hydroperoxide and tertiary butyl alcohol. It is not necessary to separate the alcohol from the hydroperoxide since the alcohol can function merely as a diluent. The molar ratio of the hydroperoxide to olefinic compound can range from 3:1 to 1:3 with 1:1 being preferred.

The reaction is carried out in the liquid phase and with liquid reactants atmospheric pressures can be used. With normally gaseous olefins such as the lower alkenes, propylene or isobutylene it is necessary to employ pressure to maintain the reactants in the liquid phase, at least, to the extent that there is some olefin in the liquid phase.

The reaction is exothermic and it is preferred to maintain the temperature between about 25° and 55° C., consequently the hydroperoxide is added at a slow rate to prevent excessive heat formation. Cooling may be employed also to control the reaction temperature.

The reaction is carried out in an aqueous system but the amount of water is not critical and the weight ratio of water to reagents can range from 1:1 to 100:1, the preferred range being from 2:1 to 15:1.

A particularly critical feature of this invention is the initial pH range of the aqueous solution, this should be above 8 and generally in the range of 8 and 12 with between 9 and 10 preferred. In order to obtain this pH and maintain a basic condition throughout the reaction, buffering agents are used. Various buffering agents can be used which will give a pH in aqueous solution in the desired range as is well known in the art. A convenient pair of compounds is sodium carbonate and sodium bicarbonate which at concentrations of about 0.1 molar give a pH in the range of 9.2 to 11.2. When sodium carbonate and sodium bicarbonate were used as shown in the runs of the Examples which follow a pH of about 9.6 to 9.7 was obtained. Other compounds can be employed, the only limitation being, of course, that they be non-reactive with the other reagents or desired products in the solution and for this reason inorganic buffering agents will usually be employed.

The preferred catalyst is osmium in its +8 valence state. In order to produce a soluble homogeneous osmium catalyst, osmium tetroxide is solubilized in water with a strong base such as sodium hydroxide. This is illustrated by the osmium catalyst employed in the following examples. The concentration of Os can range In Run 2 after the sodium carbonate, sodium bicarbonate and catalyst solution was made up in the flask, sufficient sodium hydroxide solution was added dropwise until a pH of 11.9 was attained then the remaining reagents were added as will be described. Likewise in Run 3 sufficient hydrochloric acid solution was added dropwise to give a pH of 6.8.

In each run 5.8 grams of allyl alcohol (0.1 mole) was added to the aqueous solution in the flask and then t-butyl hydroperoxide (approx. 92 percent pure, 11 ml, 0.1 mole) was added at the rate of 1 ml per 5 minutes with stirring. The reaction was exothermic and the temperature increased as shown in the Table. In each run the product was analyzed by gas-liquid chromatography to determine the amount of allyl alcohol converted and the amount of glycerol formed. The conversion of allyl alcohol in each run is shown in the Table as well as the selectivity to glycerol (based on alcohol converted) is also shown.

TABLE

| Run No. | $Na_2CO_3$ g. | $NaHCO_3$ g. | pH | Temp. °C. | Os in Conc., ppm | Wt. % Conv. of Allyl Alcohol | % Sel. of Glycerol |
|---|---|---|---|---|---|---|---|
| 1 | 2.00 | 2.30 | 9.7→9.6 | 27→48 | 700 | 95 | 89 |
| 2 | 2.00 | 2.30 | 11.9→4.7 | 27→50 | 700 | 85 | 85 |
| 3 | 2.00 | 2.30 | 6.8→3.9 | 27→50 | 700 | 80 | 63 |
| 4[a] | 2.00 | 2.30 | 9.6→9.8 | 27→50 | 700 | 41 | 91 |
| 5[a] | 2.00 | 2.30 | 9.6→9.6 | 50 | 700 | 44 | 81 |
| 6 | 0.02 | 0.11 | 9.5→7.6 | 28→50 | 34 | 98 | 96 |
| 7 | 0.02 | 0.11 | 9.7→7.9 | 28→40 | 14 | 54 | 108[b] |

[a]$O_2$ was bubbled into the reaction solution at the rate of 6 l/hr.; the amount of t-butyl hydroperoxide used was decreased from 11 ml to 5.5 ml.
[b]The reaction was then heated at 45° C. for 3 hours. It gave 70 percent conv. and 89 percent selectivity.

from 5 ppm by weight to 1000 ppm but from 25 ppm to 800 ppm by weight in the aqueous solution is preferred.

The catalyst solution was prepared by dissolving 1 gram of osmium tetroxide, $OsO_4$, in 1 liter of water made up to contain 6.3 ml of a 2.5 N NaOH solution. This gave a molar ratio of NaOH to $OsO_4$ of 2. The concentration of Os calculated to be 700 ppm by weight of Os.

The following examples are provided to show the hydroxylation of allyl alcohol to glycerol in accordance with the method of this invention.

EXAMPLE I

In each run 100 ml of an aqueous solution containing sodium carbonate, sodium bicarbonate and the osmium catalyst were placed in a four-necked flask equipped with a thermometer, a water condenser, an additional funnel, a pH electrode and a magnetic stirrer. The amounts in grams of the sodium carbonate and sodium bicarbonate are shown for each run in the Table as well as the initial and final pH. The concentration of Os is also shown. In those runs where the concentration of Os was 700 ppm (Runs 1 to 5) the sodium carbonate and sodium bicarbonate were simply added to 100 ml of the aqueous catalyst solution prepared as described above. In Run 6 the Os concentration was 34 ppm and was prepared by adding 95 ml of water to 5 ml of the stock aqueous catalyst solution (the solution prepared as described above). This gave 100 ml of aqueous solution to which the sodium carbonate and bicarbonate were added. In Run 7 the concentration of Os was 14 ppm which was obtained by adding 98 ml of water to 2 ml of the stock catalyst solution giving 100 ml of aqueous solution to which the sodium carbonate and bicarbonate were added.

It will be seen that in Run 3 where the initial pH was too low so that it was not in the preferred range, both lower conversion of alcohol and selectivity to glycerol were obtained as compared with Runs 1 to 6. Run 2 which was at the high end of the pH range showed good conversion and selectivity but not as good as for Runs 1 to 6 which were within the more preferred range.

In Runs 4 and 5 although the proper initial pH was used, oxygen was substituted for one half the hydroperoxide and low conversions of allyl alcohol resulted, and the yield of glycerol was not greater than theoretical based on the hydroperoxide consumed.

In Run 7 the concentration of catalyst was so low that additional reaction time was required to give increased conversion. The selectivities for the runs having low conversion of alcohol were found to be somewhat too high, see Run 7 for example, becasue a small error in the allyl alcohol conversion determination had a large effect on the glycerol selectivity since the glycerol was reported as based on alcohol converted. When high conversions of alcohol were obtained as in Runs 1 and 6 this error is completely negligible.

In summary Run 6 appears to be within the optimum range, both with respect to initial pH and catalyst concentrations.

EXAMPLE II

Another run was carried out in exactly the same manner of Example I except that the quantity of reactants was doubled. The aqueous solution in the flask consisted of 10 ml of the osmium catalyst stock solution, 90 ml of water, 0.02 grams sodium carbonate and 0.11 grams of sodium bicarbonate, thus the concentration of osmium was 68 ppm. To this aqueous solution was added 11.6 grams of allyl alcohol (0.2 moles) and 22 ml of tertiary butyl hydroperoxide was added slowly; the same hydroperoxide used in Example I. The temperature increased from 28° to 45° C. and the pH decreased from an initial value of from 9.9 to 7.4 It was found that 97 percent of the allyl alcohol was converted and the selectivity to glycerol was 100 percent. This run demonstrated that higher concentrations of reagents could be utilized in the reaction system.

The following Example shows the results obtained using propylene as the olefin.

EXAMPLE III

The experiment was carried out by charing 90 g. of the stock Os catalyst solution (700 ppm Os), 35 g $H_2O$, 2.0 g. $Na_2CO_3$, 2.3 g. $NaHCO_3$ and 40 ml propylene into a 300 ml titanium reactor. Thirty-nine ml of 48.5 percent t-butyl hydroperoxide in t-butyl alcohol were pumped into the reactor with stirring over a period of 2 hours. The reaction temperature rose from 26° to 43° C. After the addition of the hydroperoxide was completed, the reaction was allowed to stir for additional 30 minutes. The product was analyzed by gas liquid chromatography. The results show that the selectivity to propylene glycol based on t-butyl hydroperoxide used is 45 percent.

The embodiments of the invention in which an exclusive property is claimed are defined as follows:

1. A method for preparing polyols by the homogeneous catalytic hydroxylation of an olefinic compound selected from the group consisting of lower alkenes, allyl alcohol, oleic acid, and 1,2,3,6-tetrahydrophthalic anhydride by contacting said olefinic compound at a temperature in the range of from 25° to 55° C. with an organic hydroperoxide in an aqueous solution at an initial pH in the range of from 8 to 12 in the presence of a catalytic amount of a water soluble osmium compound in its + 8 valence state as the catalyst and wherein the concentration of osmium is in the range of from 5 ppm to 1000 ppm by weight.

2. The method according to claim 1 wherein said olefinic compound is allyl alcohol.

3. The method according to claim 1 wherein said olefinic compound is propylene.

4. The method according to claim 1 wherein said soluble osmium compound is produced by solubilizing osmium tetroxide in water with a strong base.

5. The method according to claim 4 wherein said strong base is sodium hydroxide.

6. The method according to claim 1 wherein said concentration of osmium is in the range of from 25 ppm by weight to 800 ppm by weight.

7. The method according to claim 1 wherein said organic hydroperoxide is tertiary butyl hydroperoxide.

* * * * *